United States Patent
Watanabe et al.

(10) Patent No.: US 12,275,000 B2
(45) Date of Patent: Apr. 15, 2025

(54) METHOD OF PRODUCING CATALYST OR ADSORBENT CARRIER, AND CATALYST OR ADSORBENT CARRIER

(71) Applicant: APS Japan Co., Ltd., Osaka (JP)

(72) Inventors: Takafumi Watanabe, Osaka (JP); Masao Yamaguchi, Osaka (JP); Teruo Watanabe, Osaka (JP); Hidemitsu Watanabe, Osaka (JP); Hiroyuki Watanabe, Osaka (JP)

(73) Assignee: APS JAPAN CO., LTD., Osaka (JP)

( * ) Notice: Subject to any disclaimer, the term of this patent is extended or adjusted under 35 U.S.C. 154(b) by 0 days.

(21) Appl. No.: 18/388,109

(22) Filed: Nov. 8, 2023

(65) Prior Publication Data
US 2024/0075461 A1    Mar. 7, 2024

Related U.S. Application Data

(62) Division of application No. 16/608,799, filed as application No. PCT/JP2018/020177 on May 25, 2018, now Pat. No. 11,865,512.

(30) Foreign Application Priority Data

May 30, 2017 (JP) .................... 2017-106348

(51) Int. Cl.
*B01J 21/02* (2006.01)
*B01J 20/02* (2006.01)
(Continued)

(52) U.S. Cl.
CPC ............ *B01J 21/02* (2013.01); *B01J 20/0248* (2013.01); *B01J 20/28042* (2013.01);
(Continued)

(58) Field of Classification Search
CPC ........ B01J 21/02; B01J 35/56; B01J 20/0248; B01J 20/28042; B01J 20/3071;
(Continued)

(56) References Cited

U.S. PATENT DOCUMENTS 4,066,450 A * 1/1978 Takeuchi ................ B22F 3/002
428/605
2013/0292256 A1   12/2013 Hu

FOREIGN PATENT DOCUMENTS

JP     2010-202906 A    9/2010
JP     5395253 B2       1/2014

* cited by examiner

*Primary Examiner* — James A Fiorito
(74) *Attorney, Agent, or Firm* — Kratz, Quintos & Hanson, LLP

(57) ABSTRACT

Provided is a method of producing a catalyst or adsorbent carrier and a catalyst or adsorbent carrier which can enhance a catalyst or adsorbent function, and prevent fall-off of catalyst particles or adsorbent particles. The surface of a metal base material made of aluminum or an aluminum alloy is subjected to an etching process using an etchant containing iron chloride and an oxide to convert the surface to an uneven and rough surface. The uneven and rough surface of the metal base material is subjected to an anodizing process to form a porous coating along the uneven and rough surface. A large number of catalyst or adsorbent particles are thus carried on the surface of the metal base material on which the porous coating is formed along the uneven and rough surface.

4 Claims, 8 Drawing Sheets

(51) Int. Cl.
*B01J 20/28* (2006.01)
*B01J 20/30* (2006.01)
*B01J 20/32* (2006.01)
*B01J 35/56* (2024.01)
*B01J 37/02* (2006.01)
*B01J 37/34* (2006.01)
*C23F 1/20* (2006.01)
*C25D 11/16* (2006.01)
*B01D 53/86* (2006.01)

(52) U.S. Cl.
CPC ....... *B01J 20/3071* (2013.01); *B01J 20/3204* (2013.01); *B01J 20/3217* (2013.01); *B01J 35/56* (2024.01); *B01J 37/0217* (2013.01); *B01J 37/0226* (2013.01); *B01J 37/347* (2013.01); *C23F 1/20* (2013.01); *C25D 11/16* (2013.01); *B01D 53/8668* (2013.01); *B01D 2255/20707* (2013.01); *B01D 2255/802* (2013.01); *B01D 2259/804* (2013.01)

(58) Field of Classification Search
CPC .......................... B01J 20/3204; B01J 20/3217; B01J 37/0217; B01J 37/347; C23F 1/20; C25D 11/16
See application file for complete search history.

METHOD OF PRODUCING CATALYST OR ADSORBENT CARRIER, AND CATALYST OR ADSORBENT CARRIER

TECHNICAL FIELD

The present invention relates to: a method of producing a catalyst carrier or an adsorbent carrier, in which a large number of catalyst particles or adsorbent particles are carried on the surface of a metal base material made of aluminum or an aluminum alloy; and a carrier of a catalyst or adsorbent.

BACKGROUND ART

Regarding a conventional carrier of a catalyst or adsorbent (e.g., photocatalyst filter), in which catalyst particles or adsorbent particles are carried on the surface of a metal base material, the following proposal has been made. That is, the surface of the metal base material is subjected to etching or sandblasting to make the surface uneven and rough, thereby increasing the surface area in advance. Then, catalyst particles are carried on the uneven and rough surface, whereby more catalyst particles adhere to the surface along the unevenness. Thus, the catalyst function is enhanced, and fall-off of the catalyst is prevented (refer to Patent Literatures 1 and 2, for example).

However, for the uneven and rough surface obtained through normal etching or sandblasting, as shown in FIG. 1A and FIG. 1B, the surface of a metal base material 10 is irregularly etched throughout, and therefore, recesses 20 are formed so as to overlap in a multiplex manner. When the recesses 20 are formed so as to overlap each other as described above, the depth of each recess 20 at the uneven and rough surface 2 is reduced, and the height positions of opening edges 21 of the respective recesses 20 become uneven. Therefore, as shown in FIG. 1C, there is a limit to the amount of the adhering catalyst particles 4 and the effect of preventing fall-off of the catalyst particles 4.

CITATION LIST

Patent Literature

[PTL 1] Japanese Unexamined Patent Application Publication No. 2010-202906
[PTL 2] Japanese Patent No. 5395253

SUMMARY OF THE INVENTION

Problems to be Solved by the Invention

In consideration of the above-described circumstances, an object of the present invention is to provide a catalyst or adsorbent carrier production method and a catalyst or adsorbent carrier which can enhance the catalyst or adsorbent function, and prevent fall-off of catalyst or adsorbent particles.

Solution to the Problems

As a result of the earnest investigation in view of the above circumstances, the present inventors have focused on the fact that an etching process using an etchant containing iron chloride and an oxide is performed on a base material made of aluminum or an aluminum alloy, to thereby form a large number of independently-formed recesses 20 each having an angle and being relatively deep as shown in FIG. 2B. In the uneven and rough surface 2 having the large number of recesses 20, the large number of deep recesses 20 are formed while regions R1 having the shape of the original surface of the base material 10 are partially left. Therefore, the height positions of the opening edges 21 of the respective recesses 20 are substantially equal to the position of the original surface of the base material 10.

The present inventors examined the photocatalyst effect, under the condition that photocatalyst particles 4 were carried by the uneven and rough surface 2 as shown in FIG. 2B so that the internal spaces of the respective recesses 20 were filled with the photocatalyst particles 4. Specifically, the uneven and rough surface was dipped into a slurry of photocatalyst particles to fill the recesses with the photocatalyst particles, and was dried, whereby the photocatalyst particles were carried on the uneven and rough surface as described above. Then, methylene blue was applied to the surface, dried, and irradiated with ultraviolet light. Then, remarkably high photocatalyst effect was obtained (refer to the result (FIG. 8) of catalyst effect test 1 on a sample of Comparative Example 1 described later). This result allowed the present inventors to perceive that the factor important for the catalyst effect was not the surface area of the catalyst layer on the side exposed to the external air but the amount of the carried catalyst. That is, the present inventors found that, since the uneven and rough surface used in the test was composed of the large number of deep recesses having the uniform edge portions as described above, a large amount of photocatalyst particles could be carried in the internal spaces of the respective recesses even through the simple method of dipping the surface into the slurry of photocatalyst particles described above, whereby the high photocatalyst effect was obtained.

Furthermore, the present inventors found that, in the catalyst carrier by which the high photocatalyst effect was obtained, a large gap was formed between the uneven and rough surface and the photocatalyst layer. It was considered that the large gap was caused by contraction of the catalyst layer due to evaporation of moisture during drying performed after dipping of the surface into the slurry of catalyst particles, the peeling of the metal base material due to thermal contraction thereof. That is, the gap was considered to be an adverse effect of filling the relatively deep independent recesses with the catalyst particles. Since the gap might disadvantageously cause the catalyst layer to fall off from the recesses when an impact or the like is applied, the present inventors investigated a method for preventing such peeling.

As the result of the investigation, the present inventors found the following. That is, when the surface of the metal base material 10, which had been converted to the uneven and rough surface 2, was subjected to an anodizing process to form a porous coating 3 along the uneven and rough surface 2 as shown in FIG. 2C and FIG. 2D, the degree of adhesion between the inner surfaces of the recesses 20 and the layer 40 of the catalyst particles 4 was increased, whereby the peeling was avoided. Moreover, the catalyst particles 4 were also carried on the opening edges 21 (the original surface of the metal base material) of the recesses to which the catalyst particles 4 had not been likely to adhere, whereby the amount of the carried catalyst was further increased. The present inventors considered that these findings were applicable to catalysts other than photocatalysts and to adsorbents. Thus, the present invention has been completed.

That is, the present invention includes the following features.

(1) A method of producing a catalyst or adsorbent carrier in which a large number of catalyst particles or adsorbent particles are carried on a surface of a metal base material made of aluminum or an aluminum alloy, the method including: performing an etching process using an etchant containing iron chloride and an oxide on the surface of the metal base material made of aluminum or the aluminum alloy, to convert the surface to an uneven and rough surface; performing an anodizing process on the uneven and rough surface of the metal base material, to form a porous coating along the uneven and rough surface; and causing the large number of the catalyst particles or the adsorbent particles to be carried on the surface of the metal base material on which the porous coating is formed along the uneven and rough surface.

(2) The method of producing the catalyst or adsorbent carrier according to (1), in which internal spaces of recesses at the uneven and rough surface are filled with the catalyst particles or the adsorbent particles, thereby carrying the catalyst particles or the adsorbent particles.

(3) A catalyst or adsorbent carrier in which a large number of catalyst particles or adsorbent particles are carried on a surface of a metal base material made of aluminum or an aluminum alloy, the carrier including: an uneven and rough surface formed at the surface of the metal base material made of the aluminum or the aluminum alloy; a porous coating formed along the uneven and rough surface; and the large number of the catalyst particles or the adsorbent particles carried on the surface of the metal base material on which the porous coating is formed along the uneven and rough surface, in which the uneven and rough surface has a large number of recesses with regions each having a shape of a part of an original surface of the metal base material.

(4) The catalyst or adsorbent carrier according to (3), in which internal spaces of the recesses at the uneven and rough surface are filled with the catalyst particles or the adsorbent particles, thereby carrying the catalyst particles or the adsorbent particles.

Advantageous Effects of the Invention

According to the present invention as described above, a catalyst carrier or an adsorbent carrier, which can enhance the effect of the catalyst or the adsorbent, and can prevent fall-off of a particle layer of the catalyst or the adsorbent, can be obtained.

BRIEF DESCRIPTION OF THE DRAWINGS

FIG. 3 illustrates the configuration of a metal base material as a sample of Example 2, where

DESCRIPTION OF EMBODIMENTS

Next, an embodiment of the present invention will be described in detail with reference to the accompanying drawings.

Figure 1A:
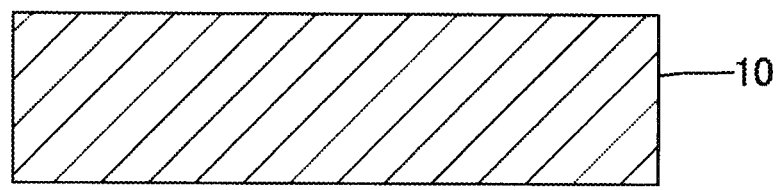
FIG. 1A to FIG. 1C illustrate a procedure for producing a conventional carrier of a catalyst or adsorbent.
Figure 1B:
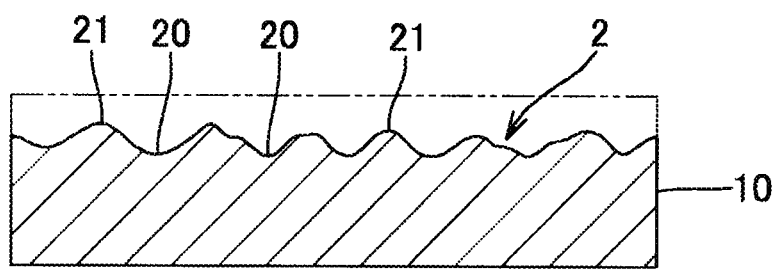
Figure 1C:
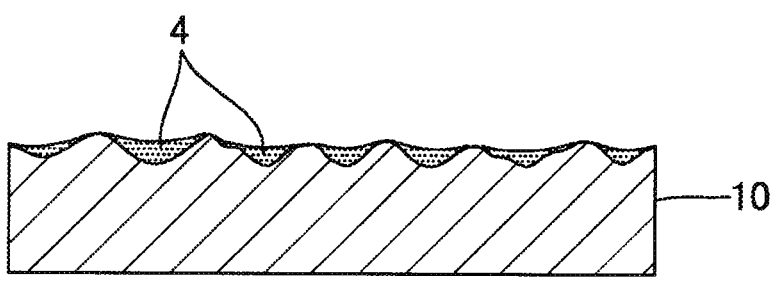
Figure 2A:
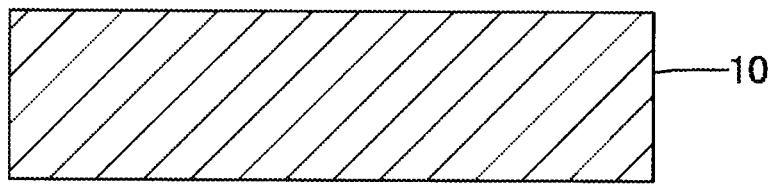
FIG. 2A to FIG. 2D illustrate a procedure for producing a carrier of a catalyst or adsorbent according to the present invention.
Figure 2B:
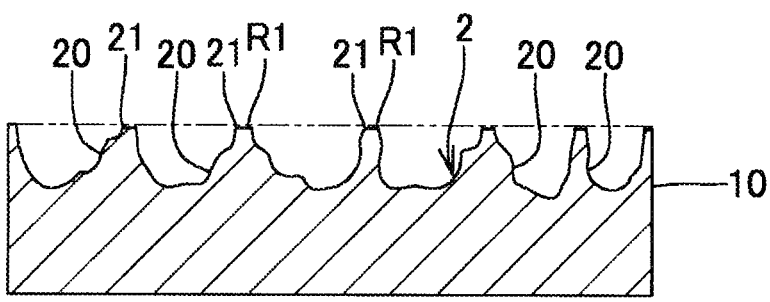
Figure 2C:
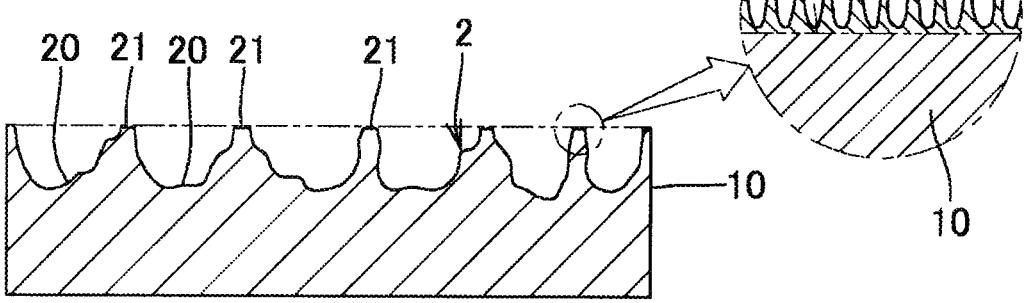
Figure 2D:
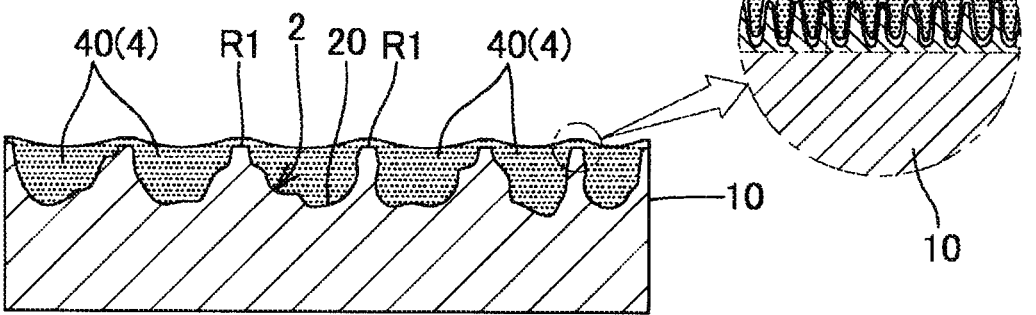

As shown in FIG. 2D, a carrier of a catalyst or adsorbent according to the present invention includes: an uneven and rough surface 2 formed at the surface of a metal base material 10 made of aluminum or an aluminum alloy; a porous coating 3 formed along the uneven and rough surface 2; and a large number of catalyst or adsorbent particles 4 carried on the surface of the metal base material 10 on which the porous coating 3 is formed along the uneven and rough surface 2. The uneven and rough surface 2 is an uneven and rough surface at which a large number of recesses 20 are formed while regions R1 having the shape of an original surface portion of the metal base material 10 are partially left.

The metal base material 10 is not particularly limited to a specific shape or configuration, and thus may naturally have a curved shape or the like in addition to a flat shape. The metal base material 10 is applicable to various shapes such as a bar shape and a tubular shape in addition to a plate shape. Various materials including casting materials (casting products, die-casting products, etc.) as well as wrought materials (pressed products, forged products, and extruded products) can be adopted as base materials.

Examples of the catalyst or adsorbent particles 4 include: photocatalyst particles such as particles of an ultraviolet excitation type photocatalyst such as titanium oxide, and particles of a visible light excitation type photocatalyst composed mainly of tungsten trioxide; particles of various catalysts, such as manganese dioxide, other than photocatalysts; and particles of various adsorbents such as activated carbon. The particle size is preferably 7 to 100 nm and more preferably 20 to 70 nm. If the particle size is too small, a decomposition substance, an adsorption substance, and light hardly reach the inside, which makes improvement of the catalyst/adsorbent function difficult.

The uneven and rough surface 2 is formed by performing an etching process using an etchant containing iron chloride and an oxide on the surface of the metal base material made of aluminum or an aluminum alloy. Thus, a rough surface having relatively deep recesses can be formed with regions having the shape of a part of the original surface, without performing masking that is a costly treatment. The etchant is preferably an aqueous solution in which the concentration of iron chloride is 0.5 to 1.5 mol/L and the concentration of an oxide is 0.5 to 1.5 mol/L. The temperature of the etchant is preferably 20 to 60° C., and the processing time is preferably 2 to 8 minutes. Thus, a larger number of deep and independent recesses can be formed. Preferably, many of the recesses have the depths of 50 to 130 nm, and more preferably, many of the recesses have the depths of 70 to 100 nm.

The porous coating 3 is formed by performing an anodizing process on the surface of the metal base material 10, which has been converted to the uneven and rough surface 2. It is preferable, in the anodizing process, that a phosphoric acid bath is used, and the specific gravity thereof is set at 0.8 to 1.5. In addition, various baths known as anodizing baths can also be adopted. The electrolytic voltage is preferably set at 20 to 50 V, and the electrolytic-bath temperature is preferably set at 8 to 20° C. The processing time is preferably 3 to 15 minutes. Through this anodizing process, the porous coating 3 having pore diameters of 30 to 200 nm and pore depths of 0.3 to 2 μm is formed.

A method for carrying the catalyst or adsorbent particles 4 is not particularly limited, but a slurry dipping method, which is relatively low in cost, is preferably adopted. The present invention can efficiently carry the catalyst particles and/or adsorbent particles through this method. The catalyst or adsorbent particles 4 are preferably carried so as to fill the internal spaces of the respective recesses 20 at the uneven and rough surface 2. In the slurry dipping method, the surface of the metal base material is impregnated with a slurry of nano-order catalyst particles or adsorbent particles. Regarding the carrying method, other dipping methods, vacuum impregnation, and sol-gel method can also be adopted. After the carrying process, air-drying or drying through sintering at a temperature of 150° C. or less is performed. In the present invention, even air-drying allows the catalyst particles and/or adsorbent particles to be carried with sufficient strength.

The embodiment of the present invention has been described above. However, the present invention is by no means limited to the above embodiment, and can be implemented in various forms without departing from the scope of the present invention.

EXAMPLES

Next, a description will be given of the results of various tests performed on samples prepared in advance as follows. The samples include: Examples (Example 1, Example 2) in which photocatalyst particles are carried on surfaces (both sides of a plate piece) having been subjected to the etching process and the anodizing process according to the present invention; Comparative Example 1 in which photocatalyst particles are carried on surfaces (both sides of a plate piece) having been subjected to only the etching process according to the present invention with omitting the anodizing process; Comparative Example 2 in which photocatalyst particles are carried on surfaces (both sides of a plate piece) having been subjected to only the anodizing process with omitting the etching process; and Comparative Example 3 in which photocatalyst particles are carried on surfaces (both sides of a plate piece) having been subjected to the conventionally general etching process.

Samples of Examples 1 and 2 and Comparative Examples 1 to 3

Figure 3A:
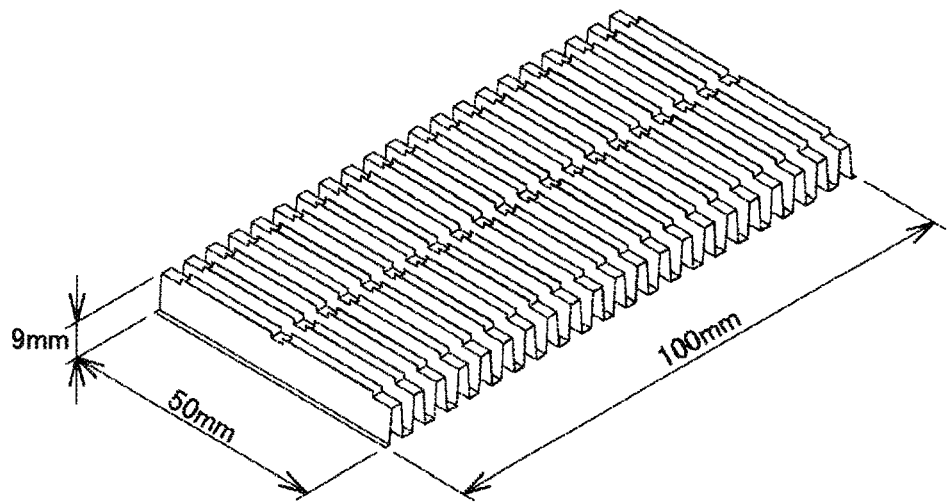
FIG. 3A is a perspective view of the entire metal base material.
Figure 3B:
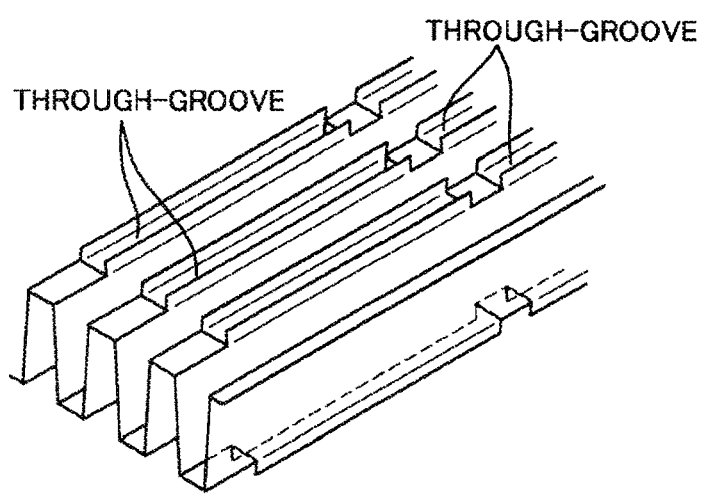
FIG. 3B is an enlarged view.
Figure 3C:
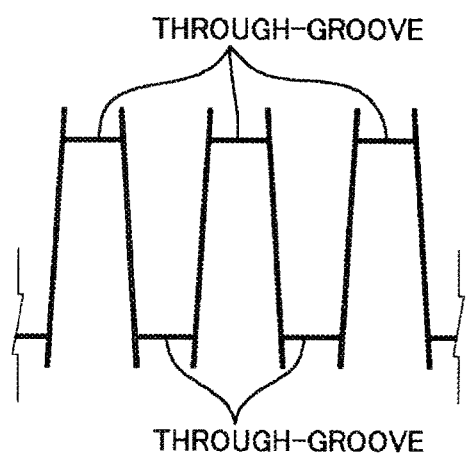
FIG. 3C is an enlarged cross-sectional view.

Regarding the samples of Example 1 and Comparative Examples 1 to 3, an aluminum plate was molded into the shape of a metal base material of the sample of Example 2 described below, and then the plate was stretched to be flat, and cut into almost the same longitudinal and lateral dimensions, thereby providing substantially flat plate pieces each serving as a metal base material. The metal base material of the sample of Example 2 was obtained as follows. That is, as shown in FIG. 3A to FIG. 3C, a 0.3 mm thick aluminum plate was press-molded into a corrugate shape, and simultaneously with the press-molding, through-grooves were formed by cutting and outwardly raising ridge portions and trough portions. This press-molded article was cut into a size of 50 mm×100 mm×9 mm, thereby providing corrugated (wavelike) plate pieces each serving as a metal base material of Example 2.

The etching processes for the samples of Examples 1 and 2 and Comparative Example 1 were performed under the same condition. The etchant was an aqueous solution that contained 1 mol/L of S-ferric chloride as ferric chloride and 1 mol/L of nitric acid as an oxide, and was set at a temperature of 32±1° C. The processing time was 3 minutes and 40 seconds.

The anodizing processes for the samples of Examples 1 and 2 and Comparative Example 2 were performed under the same conditions. The electrolytic bath of the anodizing process was a phosphoric acid bath (specific gravity: 1.2). The electrolytic voltage was set at 45 V, and the temperature of the electrolytic bath was set at 12° C. The processing time was ten minutes.

In the conventional etching process for the sample of Comparative Example 3, a 50 wt. % solution of caustic soda (NaOH) was adopted as an etchant, the temperature was set at 50° C. and the processing time was 3 minutes and 40 seconds.

For each sample, titanium-oxide particles were used as photocatalyst particles to be carried. Regarding the carrying method, a slurry containing titanium oxide particles (a slurry containing 3% of titanium-oxide particles having an X-ray particle size of 7 nm (ST-01 manufactured by ISHIHARA SANGYO KAISHA, LTD.) was used, and each sample was dipped for ten seconds into the slurry at room temperature, followed by air-drying, whereby the photocatalyst particles were carried.

Calculation of Amount of Carried Catalyst

Regarding each of the samples of Example 1 and Comparative Examples 1 to 3, the weight of the sample before and after the photocatalyst particles were carried thereon were measured, and a difference between the weights was calculated as an amount of carried catalyst.

The results are shown in Table 1.

TABLE 1

| | Amount of carried catalyst (g) |
| --- | --- |
| Example 1 | 0.53 |
| Comparative Example 1 | 0.42 |
| Comparative Example 2 | 0.16 |
| Comparative Example 3 | 0.19 |

The difference in the amount of carried catalyst between the sample of Example 1 and the sample of Comparative Example 1 is mostly caused by presence/absence of carried photocatalyst particles on the opening edges of the recesses. In the sample of Comparative Example 1 having been subjected to only the etching process according to the present invention, the amount of carried catalyst was twice or more as large as that in the sample of Comparative Example 3 having been subjected to the conventional etching. In the sample of Example 1 having been subjected to the combination of the etching process and the anodizing process according to the present invention, the amount of carried catalyst was almost three times as large as that in the sample of Comparative Example 3.

Photographing of Cross Sections

Figure 4:
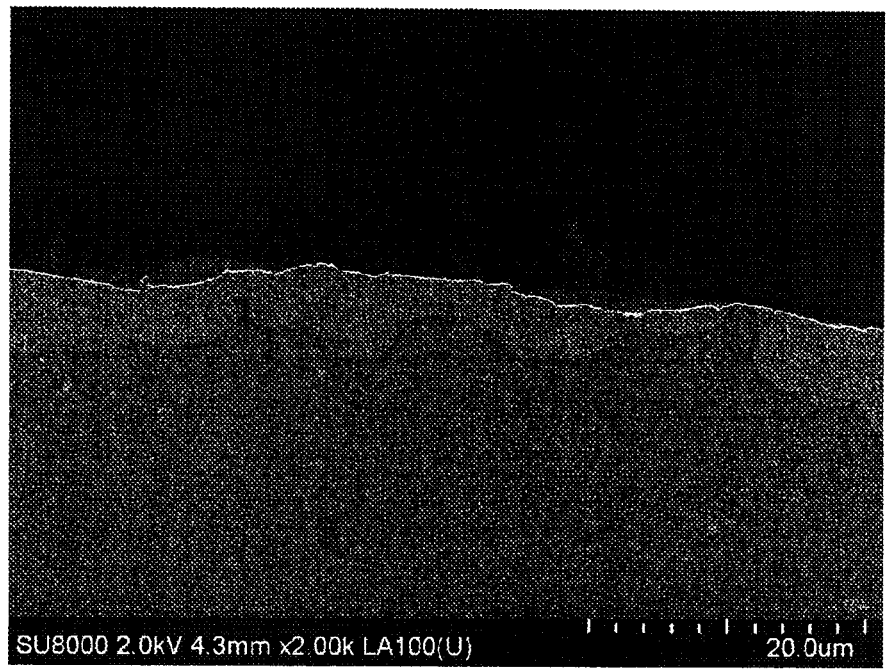
FIG. 4 is a SEM micrograph showing the cross section of a sample of Example 1.
Figure 5:
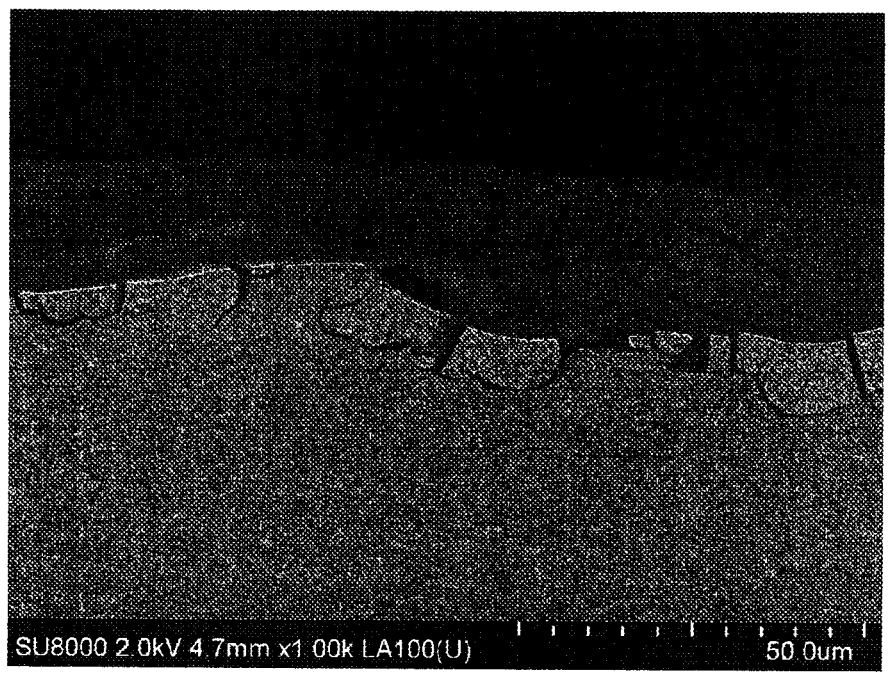
FIG. 5 is a SEM micrograph showing the cross section of a sample of Comparative Example 1.
Figure 6:
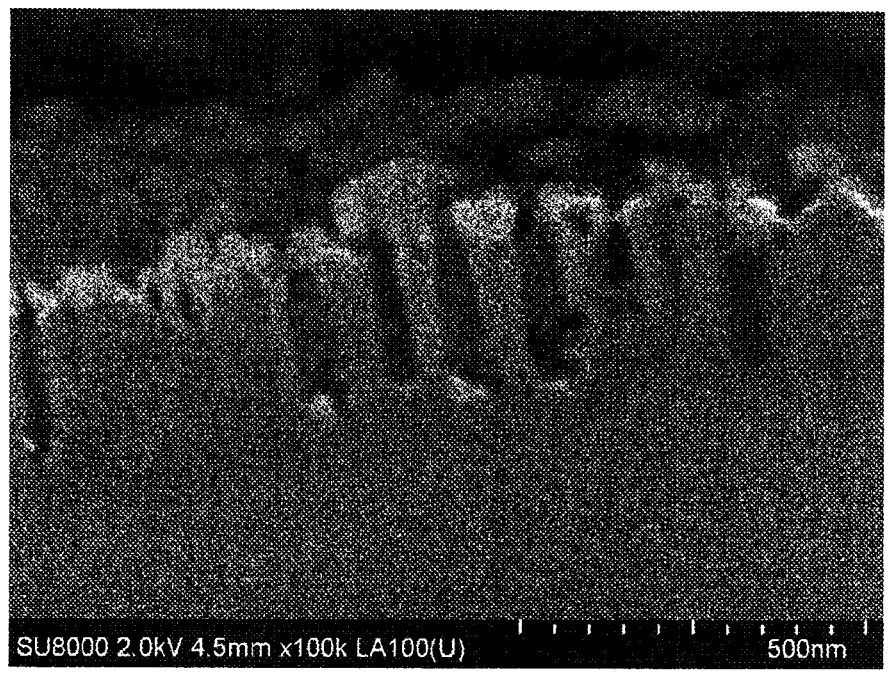
FIG. 6 is a SEM micrograph showing the cross section of a sample of Comparative Example 2.

Regarding each of the samples of Example 1, Comparative Example 1, and Comparative Example 2, the state of a cross section thereof was photographed with an SEM. FIG. 4 is an SEM micrograph showing the cross section of the sample of Example 1, FIG. 5 is an SEM micrograph showing the cross section of the sample of Comparative Example 1, and FIG. 6 is an SEM micrograph showing the cross-section of the sample of Comparative Example 2. In Example 1, as shown in FIG. 4, the recesses are deeply filled with the photocatalyst particles, and no peeling is observed between the photocatalyst particles and the metal base material. Further, it is observed that a layer of photocatalyst particles is adhered to the opening edge of each recess. Meanwhile, in Comparative Example 1 for which the anodizing process was omitted, as shown in FIG. 5, a layer of catalyst particles peels off from the surface of the base material, and is cracked into a plurality of parts. In Comparative Example 2 having been subjected only to the anodizing process, it is observed from FIG. 6 that the amount of carried catalyst is small.

Catalyst Effect Test 1

Methylene blue was applied to the surfaces (both sides of a plate piece) of each of the samples of Example 1 and Comparative Examples 1 to 3, and dried. Then, UV irradiation was performed, and the degree of disappearance of the methylene blue was photographed to confirm the photocatalyst effect. The methylene blue was obtained by mixing 0.1 g of methylene blue (Methylene Blue Trihydrate "CL52015", special grade reagent code "1133-06962", manufactured by Wako Pure Chemical Corporation) into 200 mL of dehydrated ethanol (manufactured by KENEI Pharmaceutical Co., Ltd.). After application, the methylene blue was air dried for 5 minutes, and one of the surfaces was irradiated with UV.

Figure 8:
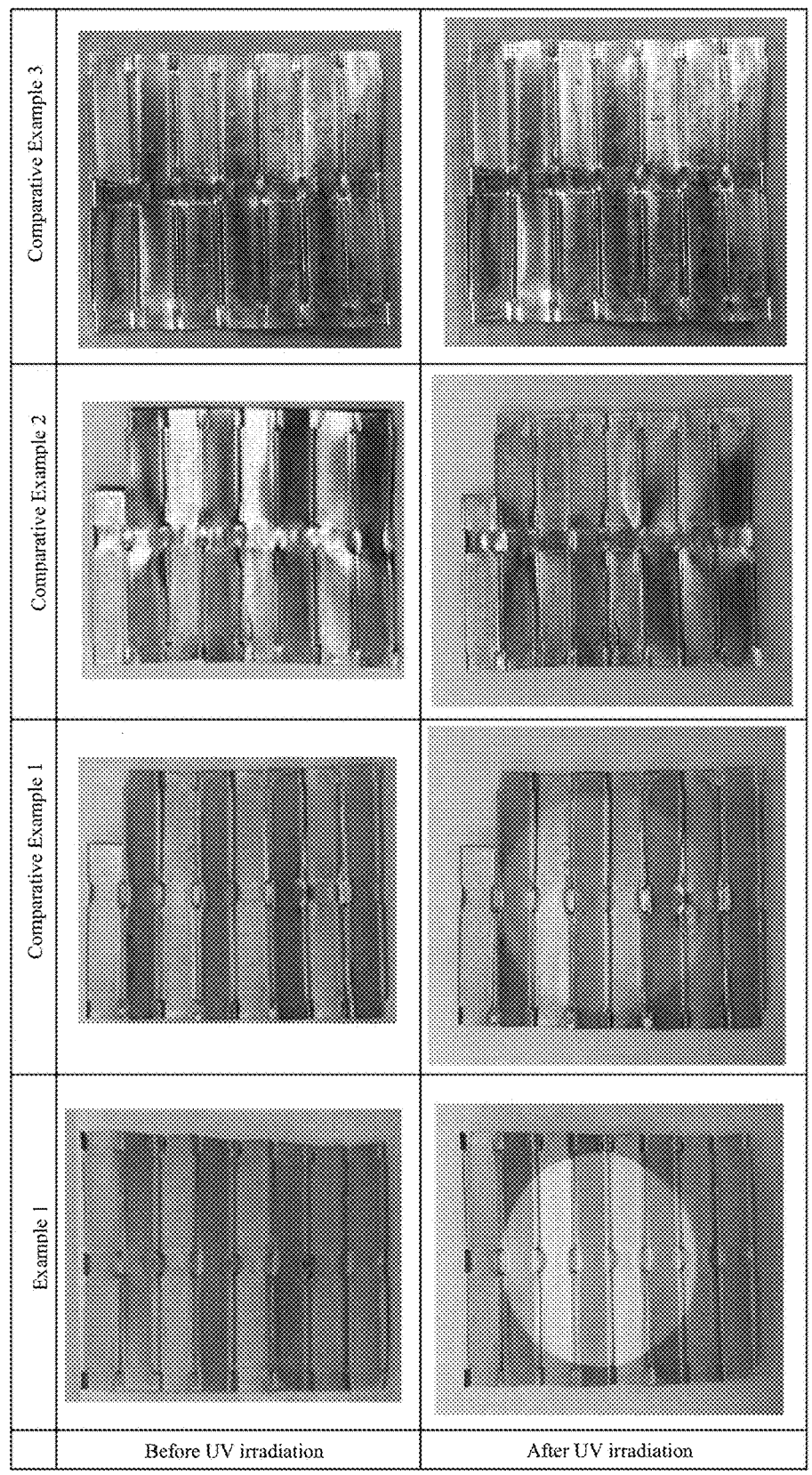
FIG. 8 is a figure comparing the results of a catalyst effect test on Example 1 and Comparative Examples 1, 2 and 3.

The UV irradiation was performed using an irradiation lamp which was composed of three UV-LEDs ("NCSU276AT" manufactured by NICHIA CORPORATION, having U365-rank peak wavelength) arranged side by side, and which had power consumption of 4.2 W. The UV irradiation was performed for 30 seconds, with the irradiation lamp placed 50 mm away from the test piece. The test results are shown in FIG. 8.

As is apparent from the results, in the samples of Example 1 and Comparative Example 1, the methylene blue in the part (circular area) irradiated with UV has almost disappeared, which means that remarkable photocatalyst effect was achieved. The methylene blue has disappeared more clearly in Example 1 than in Comparative Example 1. It is understood that this effect is caused by the difference in the amount of carried photocatalyst particles, or in other words, an increase in the amount of carried photocatalyst particles due to the anodizing process. Almost no change was observed in the methylene blue in Comparative Examples 2 and 3, which means that no photocatalyst effect was confirmed.

Tape Peeling-Off Test

Figure 9:
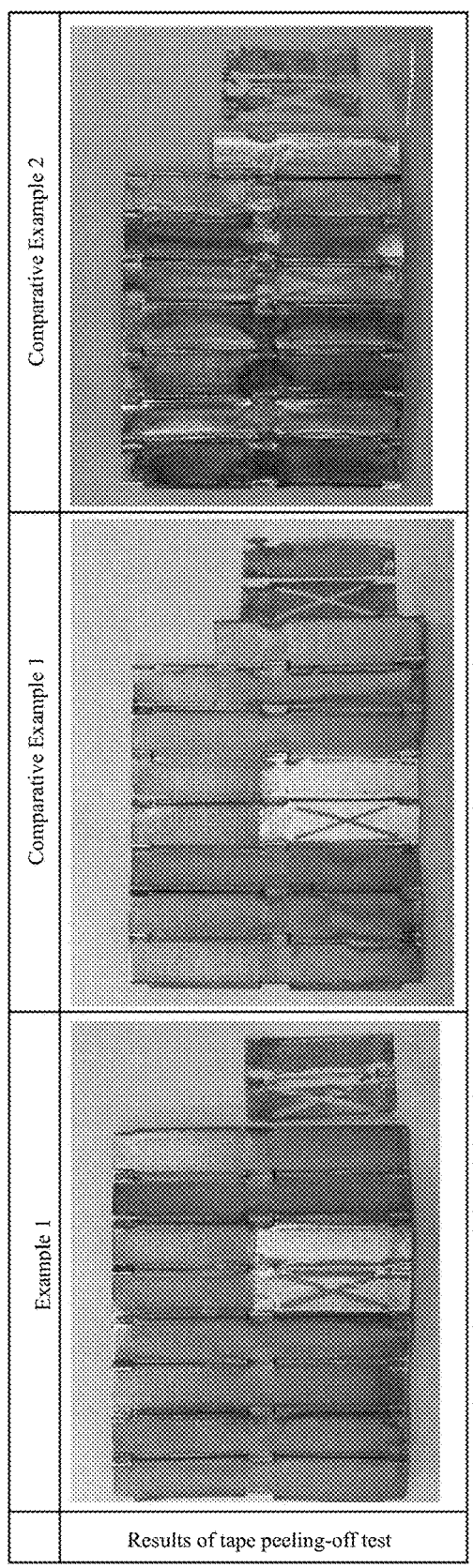
FIG. 9 is a figure comparing the results of a tape peeling-off test on Example 1 and Comparative Examples 1 and 2.

Regarding Example 1 and Comparative Examples 1 and 2, a tape peeling-off test was performed using the other surface, which was not irradiated with UV, of the surfaces of each sample to which the methylene blue was applied. A tape adopted was "Scotch (registered trademark), ultra-transparent tape S BH-18", manufactured by 3M Japan Limited. The tape was cut into pieces, each of which has the size of 18 mm×35 mm. Each piece was affixed to the surface using fingers and peeled immediately. After the catalyst particles colored by the methylene blue were peeled off together with the tape, the blue color in the corresponding part disappeared. The results are shown in FIG. 9. It is noted that X marks were made with a cutter knife to specify the tape affixed positions.

According to the result of the test, in Comparative Example 1 for which the anodizing process was omitted, most of the photocatalyst particles were clearly peeled off together with the tape. However, in Example 1 and Comparative Example 2 having been subjected to the anodizing process, more photocatalyst particles remained unpeeled. This result shows that the anodizing process improves adhesiveness of the layer of photocatalyst particles.

Catalyst Effect Test 2

Using the sample of Example 2, an acetaldehyde removal performance test was performed. The test method was based on "JIS R 1701-2$^{2016}$, Fine ceramics, Test method for air purification performance of photocatalytic materials, Part 2: Acetaldehyde removal performance".

The test was performed under specific conditions, as follows. Supply concentration of acetaldehyde: 5.13 ppm, flow rate of test gas: 1.0 L/min, water-vapor concentration: 1.56 vol. %, temperature: 23.5±1° C., light source: black light blue, FL10BLB (Toshiba)×2, UV irradiance: 10 W/m$^2$, conditions of washing and drying as pretreatment: purified-water immersion for 2 hours, followed by air drying, UV irradiance and irradiation time as pretreatment: 15 W/m$^2$, 24 hours. Since the filter-like sample was used, the test was performed in a transmission manner (manner of causing the gas to pass through the through-grooves of the filter-like sample).

Adopted test devices were as follows. Precision humidity generator: "SRG-1R-1L" manufactured by Daiichi Kagaku Inc., hydrogen flame ionization detector: "GC-2014AFF" manufactured by Shimadzu Corporation, gas blender: "GB-2C" manufactured by KOFLOC, acetaldehyde concentration analyzer: "GC-2014AFF" (lower limit of detection: 0.5 ppm) manufactured by Shimadzu Corporation, $CO_2$ concentration analyzer: "GC-2014AFF" (lower limit of detection: 0.5 ppm) manufactured by Shimadzu Corporation, gas sampler: auto-sampler incorporating a gas chromatograph. The test results are shown in Table 2 and a graph of FIG. 7. In this test, since the acetaldehyde concentration has reached the lower limit of detection (0.5 ppm), a removal percentage $R_A$ and a removal quantity $Q_A$ are calculated based on the assumption that the acetaldehyde concentration is 0.5 ppm, and "or more" is annexed to the obtained values.

TABLE 2

| | $Q_A$ (μmol/h) | $Q_C$ (μmol/h) | $R_A$ (%) | $R_C$ (%) |
|---|---|---|---|---|
| Example 2 | 12.40 or more | 25.43 | 90.3 or more | 92.5 |

$Q_A$: the quantity of acetaldehyde removed per hour (μmol/h)
$Q_C$: the quantity of $CO_2$ converted from acetaldehyde per hour (μmol/h)
$R_A$: the removal percentage of acetaldehyde (%)
$R_C$: the conversion percentage from acetaldehyde to $CO_2$ (%)

Figure 7:
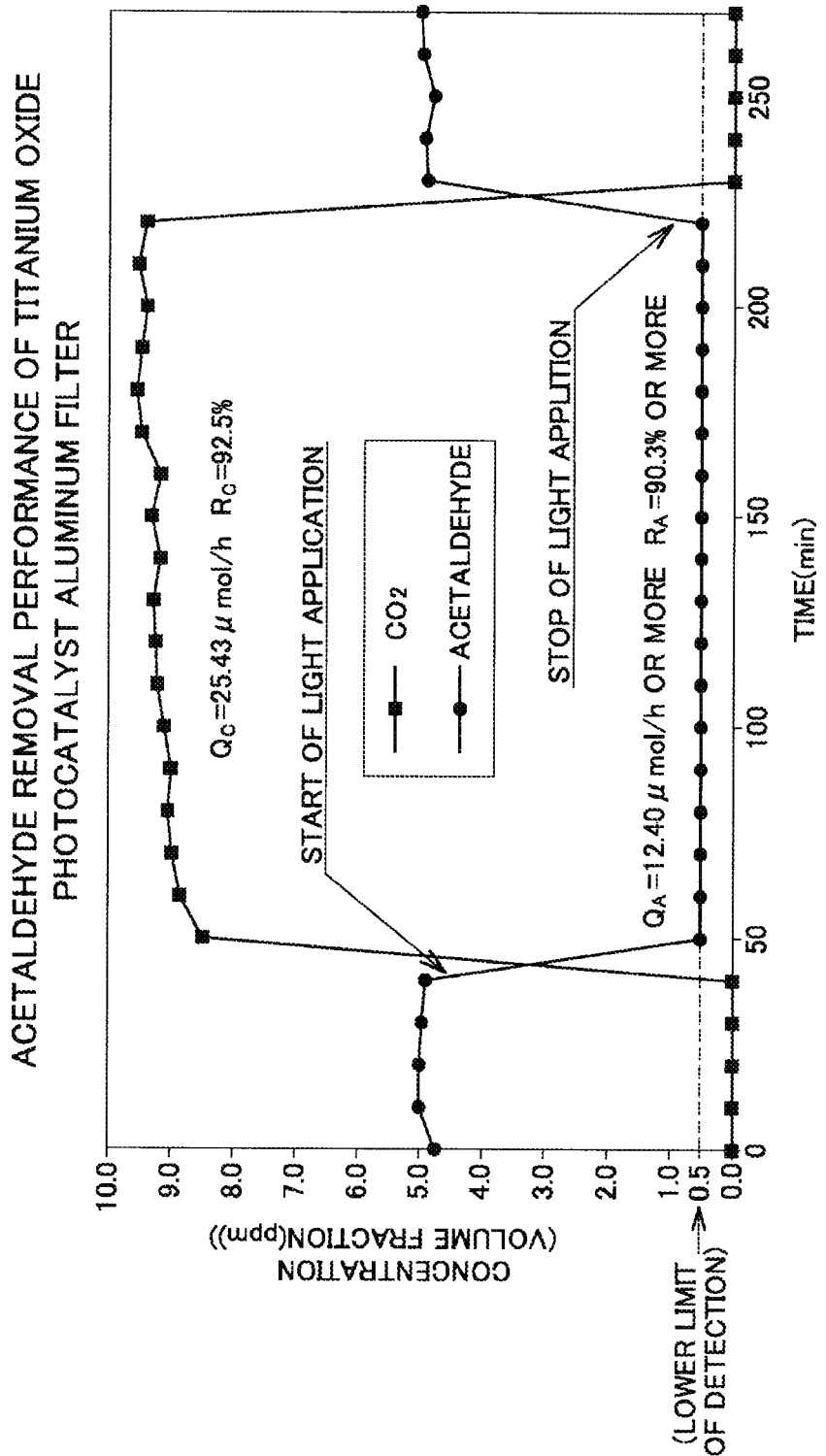
FIG. 7 is a graph showing the result of a catalyst effect test 2 using a sample of Example 2.

As can be seen from Table 2 and FIG. 7, according to the present invention, the extremely remarkable photocatalyst effects in which the removal percentage of acetaldehyde is 90.3% or more and the conversion percentage from acetaldehyde to $CO_2$ is 92.5%, can be obtained, and these excellent effects can be obtained immediately after start of the UV irradiation.

DESCRIPTION OF THE REFERENCE CHARACTERS 2 uneven and rough surface
3 porous coating
4 particle
10 metal base material
20 recess
21 opening edge
R1 region

The invention claimed is:

1. A carrier in which catalyst particles or adsorbent particles are carried on a surface of a metal base material made of aluminum or an aluminum alloy, the carrier comprising:
    an uneven and rough surface formed at the surface of the metal base material made of the aluminum or the aluminum alloy;
    a porous coating formed along the uneven and rough surface; and
    the catalyst particles or the adsorbent particles carried on the surface of the metal base material on which the porous coating is formed along the uneven and rough surface, wherein
the uneven and rough surface has recesses and has regions between the recesses in which the metal base material surface is flat, and
the carrier is a catalyst carrier or an adsorbent carrier.

2. The carrier according to claim 1, wherein
internal spaces of the recesses at the uneven and rough surface are filled with the catalyst particles or the adsorbent particles, thereby carrying the catalyst particles or the adsorbent particles.

3. The carrier according to claim 1, wherein:
the uneven and rough surface is formed by performing an etching process using an etchant containing iron chloride and an oxide on the surface of the base metal material.

4. The carrier according to claim 2, wherein:
the uneven and rough surface is formed by performing an etching process using an etchant containing iron chloride and an oxide on the surface of the base metal material.

* * * * *